US008784868B2

(12) United States Patent
Smith et al.

(10) Patent No.: US 8,784,868 B2
(45) Date of Patent: Jul. 22, 2014

(54) DEGRADABLE THERAPEUTIC DELIVERY DEVICE

(71) Applicant: Kimberly-Clark Worldwide, Inc, Neenah, WI (US)

(72) Inventors: Molly K. Smith, Atlanta, GA (US); Kelly D. Arehart, Roswell, GA (US); Lei Huang, Duluth, GA (US); Shu-Ping Yang, Alpharetta, GA (US); Yanbin Huang, Evanston, IL (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 13/785,626

(22) Filed: Mar. 5, 2013

(65) Prior Publication Data
US 2013/0245134 A1 Sep. 19, 2013

Related U.S. Application Data

(62) Division of application No. 11/405,262, filed on Apr. 17, 2006, now Pat. No. 8,399,012.

(51) Int. Cl.
A61F 6/06 (2006.01)
A61F 2/00 (2006.01)
C08L 67/02 (2006.01)

(52) U.S. Cl.
USPC .............................. 424/430; 424/426; 525/10

(58) Field of Classification Search
USPC .................................... 424/430, 426; 525/10
See application file for complete search history.

(56) References Cited

U.S. PATENT DOCUMENTS

| | | | |
|---|---|---|---|
| 4,155,991 A | 5/1979 | Schopflin et al. | |
| 4,481,353 A | 11/1984 | Nyilas | |
| 4,822,616 A | 4/1989 | Zimmermann et al. | |
| 6,020,453 A | 2/2000 | Larsson et al. | |
| 6,086,909 A | 7/2000 | Harrison et al. | |
| 6,093,394 A | 7/2000 | Chrisope | |
| 6,126,958 A | 10/2000 | Saleh et al. | |
| 6,153,209 A | 11/2000 | Vega et al. | |
| 6,159,491 A | 12/2000 | Durrani | |
| 6,264,638 B1 | 7/2001 | Contente | |
| 6,394,094 B1 | 5/2002 | McKenna et al. | |
| 6,419,913 B1 | 7/2002 | Niemiec et al. | |
| 6,537,538 B2 | 3/2003 | Zaneveld et al. | |
| 6,562,363 B1 | 5/2003 | Mantelle et al. | |
| 6,567,693 B1 | 5/2003 | Allen, Jr. | |
| 6,592,895 B2 | 7/2003 | Lang et al. | |
| 6,593,292 B1 | 7/2003 | Rothbard et al. | |
| 6,645,181 B1 | 11/2003 | Lavi et al. | |
| 6,710,220 B2 | 3/2004 | Kluger et al. | |
| 6,713,184 B1 | 3/2004 | Ferencz et al. | |
| 6,776,164 B2 | 8/2004 | Bunt et al. | |
| 6,913,759 B2 | 7/2005 | Borgman et al. | |
| 2001/0029357 A1 | 10/2001 | Blunt et al. | |
| 2002/0123644 A1* | 9/2002 | Kitai et al. | 560/330 |
| 2003/0077307 A1* | 4/2003 | Klofta et al. | 424/401 |
| 2003/0118692 A1 | 6/2003 | Wang et al. | |
| 2003/0181384 A1 | 9/2003 | Podolsky | |
| 2004/0013730 A1 | 1/2004 | Saxena et al. | |
| 2004/0120981 A1* | 6/2004 | Nathan | 424/486 |
| 2004/0142269 A1* | 7/2004 | Kotsugai et al. | 430/111.35 |
| 2004/0265355 A1 | 12/2004 | Shalaby | |
| 2005/0195651 A1 | 9/2005 | Roohparvar | |
| 2006/0067902 A1* | 3/2006 | Gotou et al. | 424/70.1 |
| 2006/0105963 A1 | 5/2006 | Yang et al. | |
| 2006/0106117 A1 | 5/2006 | Yang et al. | |

FOREIGN PATENT DOCUMENTS

| | | | |
|---|---|---|---|
| EP | 0836473 B1 | 4/1998 | |
| WO | WO 9618422 A1 | 6/1996 | |
| WO | WO 9702015 A1 | 1/1997 | |
| WO | WO 03064496 | 3/2002 | |
| WO | WO 2004100917 A1 * | 11/2004 | |
| WO | WO 2006043048 A1 * | 4/2006 | |

OTHER PUBLICATIONS

Kallinteri, Paraskevi, "Novel Functionalized Biodegradable Polymers for Nanoparticle Drug Delivery", Biomacromolecules, vol. 6, No. 4 Jul. 2005, pp. 1885-1894.
Kim, Hun Sik, "Preparation of high-molecular weight-poly(L-lactic acid)-based polymers through direct condensation polymerization in bulk state", Journal of Applied Polymer Science, vol. 100, No. 1 Apr. 5, 2005, pp. 466-472.
Knaut et al., "Alkyl Polyglycosides. A New Surfactant Class Based on Renewable Raw Material", Chimicaoggi, Sep. 1993, 6 pages.
Liu et al., J. Applied Polymer Science 2005, 98, 2033-2041.
Saeger, "Activated Sludge Degredation of Adipic Acid Esters", Applied and Environmental Microbiology, vol. 31, No. 5 May 1976, pp. 746-749.
Vermani et al., "The scope and potential of vaginal drug delivery", PSTT, vol. 3, No. 10, Oct. 2000, pp. 359-364.
Von Rybinski et al., "Alkyl Polyglycosides—Properties and Applications of a new Class of Surfactants", Angew. Chem. Int. Ed., vol. 37, 1998, pp. 1328-1345.
Wang, Yadong, "A Tough Biodegradable Elastomer", Research Article, Nature Publishing Group, 2002, pp. 602-606.
Wang et al, "In vivo degradation characteristics of poly(glycerol sebacate)", Journal of Biomedical Materials Research Part A, vol. 66A, Issue 1, Jun. 10, 2003, pp. 192-197.
Witt, Uwe, "New Biodegradable Polyester-Coplymers from commodity chemicals with favorable use Properties", Journal of Environmental Polymer Degradation, vol. 3, No. 4 1995, pp. 215-223.
International Search Report for PCT/IB2007/051157—7 pages.

* cited by examiner

Primary Examiner — Abigail Fisher
(74) Attorney, Agent, or Firm — Dority & Manning, PA

(57) ABSTRACT

A biodegradable biodelivery device is disclosed. The biodelivery device is formed from a polymer comprising the reaction product of a polyol and a polyacid. When exposed to water, the polymer degrades through hydrolysis. Of particular advantage, the polymer can be formed so as to be elastic and flexible. In one embodiment, the polymer is formed into a vaginal insert. As the polymer degrades, the polymer releases acid to a vaginal environment for decreasing the pH of the environment.

14 Claims, 2 Drawing Sheets

DEGRADABLE THERAPEUTIC DELIVERY DEVICE

CROSS REFERENCE TO RELATED APPLICATION

The present application is a divisional application of U.S. patent application Ser. No. 11/405,262 having a filing date of Apr. 17, 2006.

BACKGROUND OF THE INVENTION

Vaginal rings are devices intended to be inserted into a female in order to deliver a pharmaceutical or medicinal agent. For example, most vaginal rings are designed so as to deliver controlled amounts of a pharmaceutical or medicinal agent over an extended period of time. Vaginal rings are typically made from an elastomeric material into which the pharmaceutical or medicinal agent is incorporated. The pharmaceutical or medicinal agent is then released over time by diffusion.

In the past, various different types of drugs have been administered to patients through the use of vaginal rings. For instance, vaginal rings have been used to deliver low doses of steroids. In other embodiments, vaginal rings have been used to deliver a birth control agent, such as a spermicide.

One reoccurring problem that has been encountered in the past, however, is the ability to design a vaginal ring that will release a pharmaceutical or medicinal agent at uniform rates over a controlled period of time. Instead, many vaginal rings have a tendency to deliver higher concentrations of a medicinal or pharmaceutical agent initially and then lower concentrations as time proceeds.

Thus, a need currently exists for a vaginal ring that is better suited to releasing some type of therapeutic agent to a patient in a more uniform and controlled manner. Further, various benefits and advantages may be realized if the vaginal ring is made from a material that degrades in the vaginal environment. If the vaginal ring were made from a biodegradable material, for instance, the vaginal ring would not have to be removed after being inserted and the rate of degradation of the material may be used to control the release of any pharmaceutical, medicinal or therapeutic agents contained within the device. In fact, a biodegradable material capable of releasing a beneficial agent may have many other practical applications in addition to being used to form vaginal inserts.

SUMMARY OF THE INVENTION

In general, the present disclosure is directed to a biodelivery device made from a biodegradable polymer. In one embodiment, the biodegradable polymer can also be elastic and can be formed into any suitable shape. Once associated with the body, the biodegradable polymer degrades, such as through hydrolysis, and releases some type of therapeutic or medicinal agent. The therapeutic or medicinal agent may be encapsulated or entrained into the polymer or may actually be chemically incorporated into the polymeric structure.

In one embodiment, the biodelivery device may comprise a vaginal insert comprising an insert member having a shape configured to be inserted into a vagina. For instance, the vaginal insert may have a ring-like shape.

The insert member may be made from a biodegradable elastic polymer. The polymer can comprise a crosslinked reaction product of a polyol and a polyacid. In one embodiment, for instance, the polyol and the polyacid can both be multi-functional. For instance, in one embodiment, one of the polyol or polyacid may be at least difunctional and the other may be at least trifunctional.

The particular polyols and polyacids used to construct the biodegradable polymer can vary depending upon the desired results and, in particular, the desired physical characteristics of the resulting polymer. For instance, choosing the particular polyols and polyacids and the relative amounts can control the amount of crosslinking and can thereby control not only the elastic properties of the polymer but also the biodegradability of the polymer.

Once reacted together, the polyol and the polyacid crosslink to form ester bonds. The ester bonds degrade due to hydrolysis when exposed to water in the body, such as water present in the vaginal environment.

Suitable polyacids that may be used to construct the biodegradable polymer include carboxylic acids, such as dicarboxylic acids and tricarboxylic acids. Particular polyacids that may be used include 1,2,4-butanetricarboxylic acid, 1,3,5-pentanetricarboxylic acid, citric acid, malic acid, adipic acid, sebacic acid, succinic acid, itaconic acid, and mixtures thereof.

In one embodiment, one or more polyacids may be combined with a hydroxy acid during formation of the polymer. The hydroxy acid may comprise, for instance, an alpha-hydroxy acid. Suitable hydroxy acids include, for instance, benzoic acid, glycolic acid, lactic acid, and the like.

Polyols that may be used to construct the biodegradable polymer include, for instance, cyclic alcohols and alkyl alcohols that have at least four carbon atoms in the alkyl chain. Other polyols that may be used include various steroids and sugar alcohols.

Sugar alcohols that may be used to construct the biodegradable polymer include any suitable polysaccharide alcohols, including teritose alcohols, pentose alcohols, and hexose alcohols. Such alcohols include, for instance, xylitol, arabitol, meso-ribitol, glycerol, meso-galacitol, inositol, mannitol, sorbitol, threritol, erythritol, maltitol, lactitol, and isomers thereof.

Particular steroids that may be used include estradiol, testosterone, progesterone and isomers thereof.

When formed into a vaginal insert, the degradable polymer can be designed to degrade over a controlled length of time. For instance, the polymer can degrade over a period of time of from about 5 days to about 60 days, such as from about 15 days to about 45 days, such as from about 20 days to about 30 days. As the biodegradable polymer degrades, the polymer releases in a controlled and uniform manner a therapeutic or medicinal agent. For example, the polyacid used to form the polymer is released which decreases the pH of the vaginal environment that helps guard against the invasion of pathogenic microbes. Additionally, the polyol that is released during degradation can also provide various advantages and benefits. For example, when the polyol used to form the polymer comprises xylitol, the xylitol acts as an antimicrobial agent.

In addition to the polyacid and/or the polyol, various other therapeutic or medicinal agents can be incorporated into the polymer. For instance, the therapeutic or medicinal agent may comprise an antibacterial agent, an antimicrobial agent, an antiparasitic agent, an antibiotic, an antimetabolite, an anticancer agent, an antiviral agent, an antifungal agent, an antimycotic inflammatory agent, an anesthetic agent, an immunosuppressant, a spermicide, a humectant, an emollient, a hormone, or mixtures thereof.

In one particular embodiment, the therapeutic or medicinal agent incorporated into the biodegradable polymer is chemically bonded to the polymer. For instance, a therapeutic or medicinal agent may be selected that includes at least one hydroxy group capable of reacting with the polymer during formation of the polymer.

It should be understood that the biodegradable polymer of the present disclosure can be used to form various other biodelivery devices in addition to vaginal inserts. For instance, the polymer can be used to construct any suitable prosthetic device. Further, the polymer can be generally inserted anywhere in the body where delivery of a therapeutic or medicinal agent is desired.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
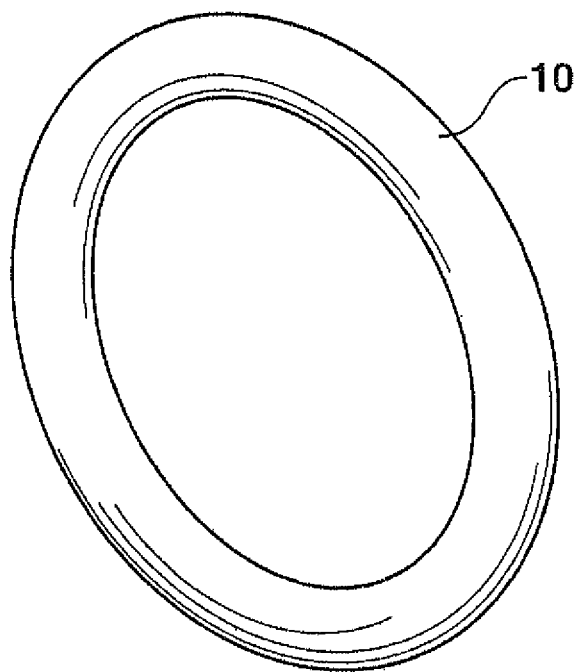
FIG. 1 is a perspective view of one embodiment of a vaginal insert made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to a biodelivery device that is made from a biodegradable polymer. Once implanted or otherwise associated with the body, the biodegradable polymer degrades at a controlled rate over time by contact with water through hydrolysis. As the biodegradable polymer degrades, the biodelivery device can be configured to release various therapeutic and/or medicinal agents. Of particular advantage, the biodegradable polymer can be made to be flexible and elastic. In this manner, the polymer can be formed or molded into any suitable shape for use in numerous different applications.

The biodegradable polymer of the present disclosure is generally formed by reacting a polyol with a polyacid. In one embodiment, the resulting polymer can be crosslinked. For example, when forming a crosslinked polymer, the polyacid and the polyol can be at least difunctional. In one embodiment, one of the polyacid or the polyol can be at least difunctional, while the other can be at least trifunctional. When the polyol is reacted with the polyacid, ester bonds are formed that are hydrolytically labile. Various biodegradable polymers have been formed that degrade due to enzymatic degradation. However, using a polymer that degrades by hydrolysis can be advantageous since tissue water content is relatively consistent among individuals and more readily available as compared to enzymes. Thus, the polymer of the present disclosure can provide greater predictability with respect to the degradation rate.

Also of particular advantage is that the biodegradable polymer of the present disclosure can be formed so as to biodegrade at a selected rate. For example, increasing or decreasing the crosslink density will slow or speed the degradation rate and make the material more rigid or flexible, respectively. Further, the monomers utilized in making the material can also be chosen to adjust its degradation rate. For example, selecting more hydrophilic monomers may translate into a material that degrades faster.

As will be described in greater detail below, as the polymer degrades, various therapeutic and/or medicinal agents can be released depending upon the particular application. For example, in one embodiment, the polyol and/or the polyacid themselves may provide a therapeutic or medicinal benefit. In other embodiments, other therapeutic or medicinal agents can be incorporated into the polymer that are released during degradation.

Although the biodegradable polymer of the present disclosure may be used in numerous applications, in one particular embodiment, the polymer can be formed into a vaginal ring for releasing acidic molecules and/or other therapeutic and medicinal agents that can help maintain a healthy vaginal environment and may prevent infection. One example of a vaginal insert, for instance, that may be made in accordance with the present disclosure is shown in FIG. 1. The vaginal insert 10 as illustrated in FIG. 1 generally has a ring-like shape. It should be understood, however, that the biodegradable polymer of the present invention can be formed into any one of numerous shapes for insertion into a female vagina. Of particular advantage, the biodegradable polymer of the present disclosure can be made so as to be flexible and elastic allowing for easy insertion and for providing comfort during use. Once inserted, the vaginal insert degrades over a controlled period of time for releasing therapeutic and beneficial agents.

There are various instances when vaginal insert 10 as shown in FIG. 1 may be needed. For example, the female vagina is naturally colonized by a variety of bacteria, yeast, and microorganisms. A normal vagina generally contains more than about $10^4$ lactobacilli per milliliter of vaginal fluid. Under normal conditions, the vagina flora provides a mildly acidic environment that helps guard against the invasion of pathogenic microbes. Unfortunately, this vaginal balance may be easily upset by a variety of external factors that ultimately lead to vaginal infection. Vaginal infection is a clinical syndrome and exists in three primary forms, i.e., bacterial vaginosis, trichomonas vaginitis ("trich") and candidal vaginitis ("yeast").

Bacterial vaginosis, for example, is a polymicrobial vaginal infection believed to be caused by an increase in the number of anaerobic organisms with a concomitant decrease in lactobacilli in the vagina. The decrease in the number of lactobacilli in the vagina has the dual effect of decreasing competition for nutrients and decreasing the amount of lactic acid present (i.e., increasing the pH). This allows for the multiplication of opportunistic pathogens in the vagina, whose growth is normally suppressed by the lactobacilli and the acidic pH of the vagina. The principal pathogen associated with bacterial vaginosis is believed to be *Gardnerella vaginalis*.

Trichomonas vaginitis (or "trick"), on the other hand, is one of the most common vaginal infections and is considered a sexually transmitted disease. Symptoms of trichomonas vaginitis include vulvar itching and odorous vaginal discharge. Trichomonas vaginitis is caused by *Trichomonas vaginalis*, a single-celled protozoan parasite not normally found in the flora of the genitourinary tract. *Trichomonas*

*vaginalis* is a flagellate protozoa that is pear-shaped and about the size of a white blood cell. These motile cells have four flagellae and a single nucleus.

Further, the yeast *Candida albicans* causes the disease known as candidiasis (or "thrush"), as well as vulvitis (or "vulval" infection). *Candida albicans* is present in most humans as a harmless commensal organism. Problems arise, however, when a person experiences a loss of normal bacterial flora. In severely immune compromised patients, for example, *Candida albicans* infection may spread throughout the body and cause systemic infections.

Vaginal rings made according to the present disclosure are capable of releasing therapeutic or medicinal agents capable of treating or preventing vaginal infections. As described above, the vaginal ring is made from a biodegradable polymer formed from the reaction product of a polyacid and a polyol. Of particular advantage when constructing a vaginal ring, as the polymer degrades, the polyacid is released thereby lowering the pH of the vaginal environment. Lowering the pH helps maintain healthy vaginal pH and encourages the growth of beneficial flora, which assists in preventing infection. Further, other therapeutic and/or medicinal agents can be incorporated into the polymer for providing other benefits.

The particular polyacid and/or polyol that are reacted together to form the biodegradable polymer can vary depending upon the particular application and the desired results. In general, polyacids and polyols are selected that have at least two functional groups.

Polyacids that may be used to form the biodegradable polymer include, in general, any suitable hydroxy acid. For instance, in one embodiment, the polyacid may be a carboxylic acid, such as a dicarboxylic acid or a tricarboxylic acid.

Particular polyacids that may be used to construct the polymer include citric acid, malic acid, adipic acid, sebacic acid, succinic acid, itaconic acid, glutaric acid, pimelic acid, suberic acid, azelaic acid and the like. Other examples of polyacids include alkyl dicarboxylic acids and alkyl tricarboxylic acids such as 1,2,4-butanetricarboxylic add or 1,3,5-pentanetricarboxylic acid. Further, a mixture of polyacids may also be used in forming the polymer.

Various polyols can also be used in forming the biodegradable polymer depending upon the particular application. Polyols that may be used in forming the polymer include diols, triols, and the like. In one embodiment, for instance, the polyol may comprise an alkyl polyol such as an alkyl triol or an alkyl diol. The alkyl polyol can have at least four carbon atoms in the alkyl chain. Suitable examples include, for instance, butanetriol.

In an alternative embodiment, the polyol may comprise a cyclic polyol, such as a cyclic diol or a cyclic triol. Example of a suitable cyclic compounds include cyclohexane diol and inositol. In another embodiment, a polymeric glycol may be used. Examples of suitable polymeric glycols that may be used to construct the device are polyethylene glycol and polypropylene glycol as well as polaxomers like the Pluronic® line (available from BASF).

In still another embodiment, the polyol incorporated into the biodegradable polymer may comprise a sugar alcohol. Sugar alcohols may provide various benefits and advantages to the vaginal environment as the polymer degrades. Sugar alcohols are hydrogenated forms of sugar that may be modified into compounds that retain the basic configuration of saccharides, but with different functional groups. Suitable sugar alcohols may include pentose alcohols (e.g., D-xylitol, D-arabitol, meso-ribitol (adonitol), and isomers thereof), hexose alcohols (e.g., glycerol, meso-galacitol (dulcitol), inositol, D-mannitol, D-sorbitol, and isomers thereof), and teritose alcohols (e.g., threritol, erythritol, and isomers thereof). For example, the chemical structures of xylitol, arabitol and adonitol are as follows:

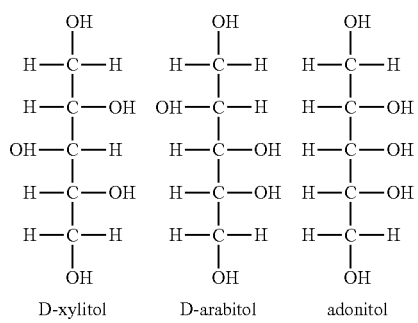

In one particular embodiment, for instance, the biodegradable polymer is formed using xylitol as the polyol. Exogenous xylitol is metabolized to glucose and glucogen or pyruvate and lactate in the liver. Many bacteria, however, are unable to utilize xylitol as an energy source, and as such, its presence may be harmful to some bacteria despite the availability of an alternative energy source, such as glucose. For instance, it is known that xylitol may reduce the growth of *Streptococcus mutans, Streptococcus salivarius, Streptococcus sanguis, Lactobacillus casei* and some strains of *Escherichia coli, Saccharomyces cerevisae* and *Salmonella typhii*. Although the anti-microbiological mechanism of xylitol is not fully understood, the present inventors believe that xylitol may be transported into a pathogen to disrupt its metabolic process and/or gene expression capabilities. For instance, xylitol may be phosphorylated through the constitutive fructose phosphotransferase system that regulates many metabolic processes and gene expression in bacteria. In addition, because bacteria adhere to host cells through carbohydrate-binding proteins, extracellular xylitol may also disturb the binding process by acting as a receptor analogue for the host cell, which could result in decreased adherence.

In addition to xylitol, other sugar alcohols may also provide various advantages and benefits. For instance, erythritol and mannitol may also inhibit or destroy various microorganisms or prevent microorganisms, such as bacteria, from adhering to lining membranes. Further, glycerol may not only have some antimicrobial properties but also is a lubricant moisturizer.

In addition to sugar alcohols, in another embodiment, the polyol used to form the biodegradable polymer may comprise a steroid. For instance, a hormone having hydroxy groups like estradiol and testosterone may be used. The chemical structures of estradiol and testosterone are as follows:

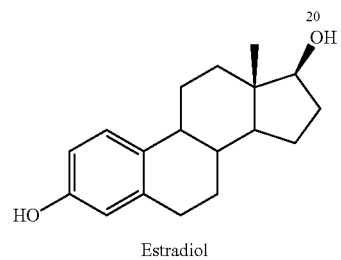

Estradiol

-continued

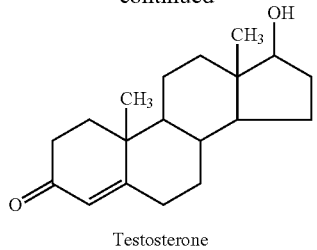

Testosterone

Similar to the polyacid, when forming the biodegradable polymer, one or more polyols may be used in constructing the polymer. For example, there may be some benefits in using more than one sugar alcohol to form the biodegradable polymer.

In one embodiment, the polyacid and the polyol may be further combined with a hydroxy acid. The hydroxy acid may react with the other components to form the polymer.

In general, any suitable hydroxy acid, such as an alpha-hydroxy acid may be used. Particular examples of hydroxy acids include lactic acid, benzoic acid, glycolic acid, and mixtures thereof.

Once formed into a vaginal ring and inserted into a vaginal environment, the period of time it takes for the vaginal ring of the present disclosure to degrade can vary depending upon the desired result. For instance, vaginal rings made according to the present invention can degrade over a period of time of from about 10 days to about 90 days, such as from about 15 days to about 60 days, such as from about 20 days to about 45 days. The amount of time it takes for the vaginal ring to degrade will depend upon the size of the ring and the manner in which the polymer is constructed. For instance, selecting the polyacid and the polyol along with the amount of crosslinking that occurs in the polymer can have a significant impact upon the length of time it takes for the polymer to degrade.

For example, increasing the crosslinking density of the biodegradable polymer increases the amount of time it takes for the polymer to degrade. For example, when the functional groups contained on the polyol and the functional groups contained on the polyacid are in stoichiometric amounts during formation of the polymer, the crosslinking density is at a maximum. In order to decrease the crosslinking density, greater amounts of one of the reactants may be used. For instance, the polyol or the polyacid may be present in an amount greater than about 10%, such as in an amount greater than about 20% in excess of the stoichiometric amount based upon the number of functional groups. In general, the crosslink density of the polymer may be from about 5% to about 100%, such as from about 10% to about 50%.

In addition to crosslinking density, choosing the particular reactants may also have an effect on degradation. For instance, using reactants that are more hydrophilic will create a polymer that will degrade faster.

Choosing the particular reactants in particular amounts can also affect the physical properties of the resulting polymer. In general, when constructing a vaginal ring, the polymer should be biocompatible and should be flexible and elastic so that it may be easily inserted and will return to its original shape once placed in position. For instance, the polymer can have a maximum elongation of greater than about 100%, such as greater than about 200%, such as greater than about 300%. The polymer can also have a modulus of less than about 5 MPa, such as less than about 3 MPa, such as less than about 0.5 MPa. The tensile strength of the polymer, on the other hand, may be greater than about 0.5 MPa, such as greater than about 1 MPa.

In addition to the polyacid and the polyol, various other therapeutic and/or medicinal agents can be incorporated into the biodegradable polymer. The therapeutic or medicinal agent can be incorporated into the polymer during its formation in any suitable manner. For instance, the therapeutic or medicinal agent can be uniformly mixed with the polymer, can form a coating on the polymer, or can form a deposit or pocket within the polymer. For example, further therapeutic and/or medicinal agents can be incorporated into the polymer in a manner in which the release of the therapeutic or medicinal agent can be controlled.

In one particular embodiment, the therapeutic or medicinal agent can be chemically reacted with the biodegradable polymer. For instance, any suitable therapeutic and/or medicinal agent containing a hydroxy group may react with the polyol and polyacid during formation of the polymer. Examples of therapeutic and/or medicinal agents that can be incorporated into the polymer include, for instance, antibacterial agents, antimicrobial agents, antiparasitic agents, antibiotics, antihistamines, decongestants, antipruritics, antimetabolites, antiglaucoma agents, anti-cancer agents, antiviral agents, antifungal agents, antimycotics, anti-inflammatory agents, anti-diabetic agents, anesthetic agents, anti-depressant agents, analgesics, anti-coagulants, opthalmic agents, angiogenic factors, immunosuppressants, anti-allergic agents, spermicides, humectants and emollients, hormones, and so forth. Example of suitable therapeutic or medicinal agents for condensation polymerization with polyacids are those have —OH end groups. Numerous such compounds are known to those of skill in the art and described, for example, in *The Pharmacological Basis of Therapeutics*, Hardman, Limbird, Goodman & Gilman, McGraw-Hill, New York, (1996), as well as U.S. Pat. Nos. 6,419,913 to Niemiec, et al.; 6,562,363 to Mantelle, et al.; 6,593,292 to Rothbard, et al.; 6,567,693 to Allen, Jr.; and 6,645,181 to Lavi, et al., all of which are incorporated herein in their entirety by reference thereto for all purposes.

As can be appreciated, the above therapeutic and/or medicinal agents can be incorporated into biodegradable polymer in order to form a vaginal ring or may be incorporated into any other suitable biodelivery device.

One particularly useful class of therapeutic agents for vaginal applications is anti-microbial agents that prevent and treat vaginal infection caused by overgrow of *Gardnerella* (e.g., *Gardnerella vaginalis*), *Candida* (e.g., *Candida albicans*), and/or *Trichomonas* (e.g., *Trichomonas vaginalis*) pathogens. Desirably, such antimicrobial efficacy is achieved without substantially inhibiting the growth of *Lactobacillus acidophilus*.

In addition, long chain alcohols may also be incorporated into the biodegradable polymer as desired. Examples of long chain alcohols include, but are not limited to, decyl alcohol, cetyl alcohol, stearyl alcohol, lauryl alcohol, myristyl alcohol, oleyl alcohol, and so forth. The "alkyl group" of the long chain alcohols is generally a linear alkyl group (i.e., a straight chain alcohol residue), which typically has an even number of carbon atoms. The long chain alcohols desirably include alkyl groups having 8 to 20 carbon atoms, in some embodiments 8 to 14, and in some embodiments, 9 to 12.

In one particular embodiment, a hydroxy acid may be incorporated into the biodegradable polymer as described above that provides therapeutic or medicinal value to the product. For example, lactic acid may be incorporated into the biodegradable polymer. Lactic acid is a monocarboxylic acid and if desired can be reacted with the polymer during its formation. As the polymer degrades the lactic acid will be released. Lactic acid is a natural regulator of vaginal pH and is relatively hydrophilic.

In addition to lactic acid, other hydroxy acids may also provide various benefits. For instance, glycolic acid may serve as a skin conditioner.

Other therapeutic agents that may be of interest include bisphosphonates like risedronate, alendronate and ibandronate that may be useful as osteoporosis therapies, gonadotropin-releasing hormone antagonists and Danazol, both of which may be used when endometriosis is diagnosed and prostaglandins and oxytocin, which function as labor inducers.

Although the biocompatible polymer of the present disclosure has been discussed above in relation to a vaginal ring, it should be understood that the polymer can be used in any suitable biodelivery device. In particular, the polymer can be molded or formed into any suitable shape for delivering a therapeutic and/or medicinal agent to any part of the body. In other applications, for instance, the biodelivery device may be placed in association with the body and may degrade for releasing therapeutic and/or medicinal agents to the sinus system or to the digestive tract. The biodegradable polymer may also be used in conjunction with a wound dressing for delivering various agents to a wound or surgical site. In still another embodiment, the biodelivery device may be used as a biodegradable dental implant or as a biodegradable prosthetic device for being implanted into any suitable part of the body. As described above, the physical characteristics of the polymer can be controlled for any desired application.

The present disclosure may be better understood with respect to the following examples:

EXAMPLE NO. 1

In this example, a biodegradable polymer was synthesized via polycondensation of 0.15 mol each of glycerol and sebacic acid. To begin the reaction, the sebacic acid was placed into a 3-neck flask that was held in a silicone oil bath at 135° C. until the acid melted, at which point the glycerol was added to the flask. The reaction mixture was maintained at this temperature and stirred under a flow of nitrogen for 20 hours. Then the contents of the flask were transferred to a cylindrical metal container and placed in a vacuum oven at 135° C. and −95 kPa for 30 hours to remove the water produced by the reaction and drive it to completion. The resulting material was translucent to transparent, slightly yellowish in color and was flexible and elastic.

EXAMPLE NO. 2

In the example, a biodegradable polymer was synthesized via polycondensation of 0.05 mol xylitol and 0.0825 mol sebacic acid. To begin the reaction, the sebacic acid was placed into a 3-neck flask that was held in a silicone oil bath at 135° C. until the acid melted, at which point the xylitol was added to the flask. The reaction mixture was maintained at this temperature and stirred under a flow of nitrogen for 24 hours. Then the contents of the flask were transferred to a cylindrical metal container and placed in a vacuum oven at 135° C. and −95 kPa for 40 hours to remove the water produced by the reaction and drive it to completion. The resulting material was translucent to transparent, slightly yellowish in color and was flexible and elastic.

EXAMPLE NO. 3

Another example of a biodegradable polymer was synthesized via polycondensation of 0.025 mol xylitol, 0.041 mol glycerol and 0.0825 mol sebacic acid. To begin the reaction, the sebacic acid was placed into a 3-neck flask that was held in a silicone oil bath at 135° C. until the acid melted, at which point the xylitol was added to the flask. The reaction mixture was maintained at this temperature and stirred under a flow of nitrogen for 24 hours. Then the contents of the flask were transferred to a cylindrical metal container and placed in a vacuum oven at 135° C. and −95 kPa for 40 hours to remove the water produced by the reaction and drive it to completion. The resulting material was translucent to transparent, slightly yellowish in color and was flexible and elastic.

EXAMPLE NO. 4

In this example, samples of the biodegradable polymers formed in Examples 1 through 3 above were tested. In particular, the three materials having dimensions of 12×6×4 mm were prepared in order to characterize their degradation kinetics. When incubated at 37° C. in 3 mL simulated vaginal fluid (SVF: 3.51 g/L NaCl, 1.40 g/L KOH, 0.222 g/L $Ca(OH)_2$, 0.018 g/L bovine serum albumin, 2.00 g/L lactic acid, 1.00 g/L acetic acid, 0.16 g/L glycerol, 0.4 g/L urea and 5.0 g/L glucose) having a pH of 4.2 or 6.0, these samples of the three materials degraded to lose approximately 10% of their initial mass over the period of 1 month. This relatively slow degradation rate is desirable for a number of potential applications of the material. The materials swell by approximately 2-3% of their initial size in aqueous solution. This small degree of swelling is an important characteristic for materials that will be implanted or inserted into the body, such that devices made from the material do not deform significantly from their initial size and shape.

Figure 2:
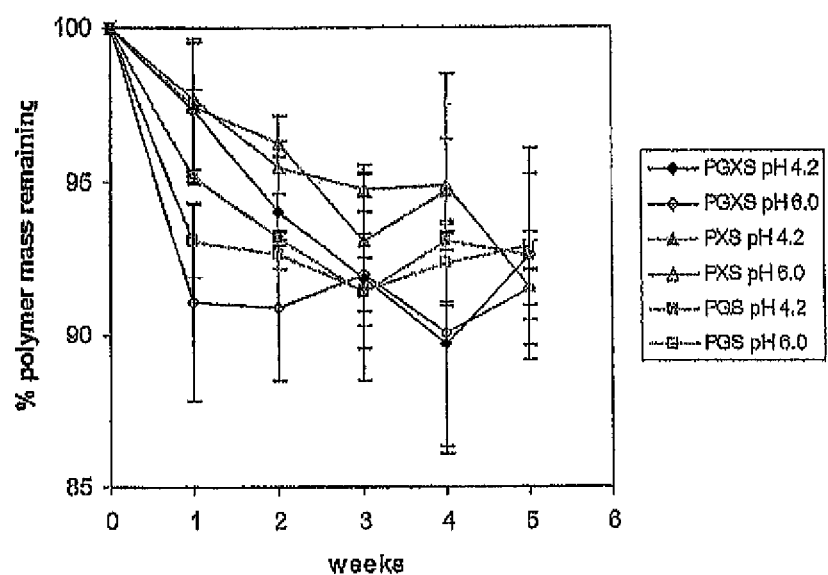
FIG. 2 is a graphical representation of various results obtained as described in the examples below. Plot showing mass loss from polymer samples over time during incubation in simulated vaginal fluid. PGXS is the polymer of glycerol, xylitol and sebacic acid; PXS is the polymer of xylitol and sebacic acid; PGS is the polymer of glycerol and sebacic acid, and the pH indicated is the intitial pH of the SVF in which the samples were incubated.

The results of the degradation study are illustrated in FIG. 2.

When samples of the three example materials were incubated for 24 hours at 37° C. in SVF having a pH of 7.0, the fluid pH decreased by 1.7-1.9 units. When incubated in this manner in SVF with an initial pH of 6.0, the fluid pH decreased by 0.6-1.0 units. When incubated in SVF with an initial pH of 5.0, the fluid pH decreased by 0.2-0.3 units. However, degradation of the samples did not have a significant effect on pH when the initial pH of the SVF was 4.2. As this example demonstrates, the extent of pH reduction may be tuned to bring the pH to an appropriate level for the particular application, but not to a lower level than desired. These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A biodelivery device comprising a biodegradable polymer, the biodegradable polymer comprising a crosslinked reaction product of a polyol and a polyacid, wherein the polyol and polyacid are both multi-functional, the polyol comprising a cyclic alcohol, an alkyl alcohol that is at least trifunctional having at least four carbon atoms in the alkyl chain, a steroid, isomers thereof or mixtures thereof, the biodegradable polymer containing ester bonds that degrade by hydrolysis, wherein the biodelivery device is a vaginal insert.

2. The biodelivery device as defined in claim 1, wherein the polyol comprises butanetriol.

3. The biodelivery device as defined in claim 1, wherein the polyacid comprises citric acid, malic acid, adipic acid, sebacic acid, succinic acid, itaconic acid, glutaric acid, pimelic acid, suberic acid, azelaic acid or mixtures thereof.

4. The biodelivery device as defined in claim 1, wherein the biodelivery device further comprises a therapeutic or medicinal agent in addition to the crosslinked reaction product of the polyacid and the polyol.

5. The biodelivery device as defined in claim 4, wherein the therapeutic or medicinal agent comprises an antibacterial agent, an antimicrobial agent, an antiparasitic agent, an antibiotic, an antihistamine, a decongestant, an antipruritic, an antimetabolyte, an antiglaucoma agent, an anti-cancer agent, an antiviral agent, an antifungal agent, an antimicotic inflammatory agent, an antidiabetic agent, an aesthetic agent, an anti-depressant, an analgesic, an anticoagulant, an ophthalmic agent, an angiogenic factor, an immunosuppressant, an anti-allergenic agent, a spermicide, a humectant, an emollient, a hormone, or mixtures thereof.

6. The biodelivery device as defined in claim 4, wherein the therapeutic or medicinal agent includes hydroxy groups that react with the biodegradable polymer during formation of the biodegradable polymer, 7. The biodelivery device as defined in claim 6, wherein the therapeutic or medicinal agent comprises lactic acid or an alkyl alcohol having from about 8 carbon atoms to about 20 carbon atoms in the alkyl chain.

8. The biodelivery device as defined in claim 1, wherein the biodegradable polymer comprises a crosslinked reaction product of the polyol, the polyacid, and a hydroxy acid.

9. The biodelivery device as defined in claim 1, wherein the polyol is a steroid and comprises estradiol, testosterone, progesterone, or isomers thereof.

10. The biodelivery device as defined in claim 1, wherein the polyol is at least trifunctional.

11. The biodelivery device as defined in claim 1, wherein the polyacid is at least trifunctional.

12. The biodelivery device as defined in claim 1, wherein the polyol comprises cyclohexane diol.

13. The biodelivery device as defined in claim 1, wherein the biodelivery device is configured to completely degrade when placed in a vaginal environment for a period of time from about 10 days to about 60 days.

14. the biodelivery device as defined in claim 1, wherein the insert member is configured to reduce the pH of a vaginal environment as the polymer biodegrades.

* * * * *